(12) United States Patent
Onishi

(10) Patent No.: US 9,029,151 B2
(45) Date of Patent: May 12, 2015

(54) METHOD FOR DIVIDING SOMATIC EMBRYO MASS

(75) Inventor: Noboru Onishi, Sakura (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/140,303

(22) PCT Filed: Dec. 17, 2009

(86) PCT No.: PCT/JP2009/071516
§ 371 (c)(1),
(2), (4) Date: Aug. 30, 2011

(87) PCT Pub. No.: WO2010/071229
PCT Pub. Date: Jun. 24, 2010

(65) Prior Publication Data
US 2011/0307975 A1    Dec. 15, 2011

(30) Foreign Application Priority Data

Dec. 17, 2008    (JP) ................................ 2008-321557

(51) Int. Cl.
*C12N 5/00* (2006.01)
*A01H 4/00* (2006.01)
*C12N 5/04* (2006.01)

(52) U.S. Cl.
CPC .................. *A01H 4/00* (2013.01); *A01H 4/003* (2013.01); *C12N 5/04* (2013.01); *A01H 4/005* (2013.01)

(58) Field of Classification Search
CPC ......... A01H 1/00; A01H 4/003; A01H 4/008; A01H 4/00; C12M 3/00; C12N 15/00; C12N 5/04; B02B 3/12
USPC .......................................................... 435/420
See application file for complete search history.

(56) References Cited

U.S. PATENT DOCUMENTS 5,294,549 A * 3/1994 Pullman et al. ............... 435/422

FOREIGN PATENT DOCUMENTS

| JP | 315326 | | 1/1991 |
|---|---|---|---|
| JP | 05-192051 A | | 8/1993 |
| JP | 6261643 | * | 9/1994 |
| JP | 731310 | | 2/1995 |
| JP | 2003009689 | | 1/2003 |

OTHER PUBLICATIONS

Rodriguez et al. Mechanical purification of torpedo stage somatic embryos of *Daucus carota* L. Paint Cell Tissue and Organ Culture 23: 9-14 1990.*
Office Action for Japanese Application No. 2008-321557 dated Aug. 13, 2013.
Takashi Noguchi, "An efficient somatic embryogenesis in Udo (*Aralia cordata* Thumb.)", Bulletin of the Tokyo Metropolitan Agricultural Experiment Station, 1997, pp. 1-8, vol. 27.

* cited by examiner

*Primary Examiner* — Annette Para
(74) *Attorney, Agent, or Firm* — Sughrue Mion, PLLC

(57) ABSTRACT

The present invention relates to a method for inducing a single somatic embryo, which comprises physically dividing a plant somatic embryo mass, and to a method for mass-propagation of a plant comprising inducing a large number of single somatic embryos from a somatic embryo mass according to the above method and germinating the somatic embryos.

2 Claims, 18 Drawing Sheets
(16 of 18 Drawing Sheet(s) Filed in Color)

METHOD FOR DIVIDING SOMATIC EMBRYO MASS

CROSS REFERENCE TO RELATED APPLICATIONS

This application is a National Stage of International Application No. PCT/JP2009/071516 filed Dec. 17, 2009, claiming priority based on Japanese Patent Application No. 2008-321557, filed Dec. 17, 2008, the contents of all of which are incorporated herein by reference in their entirety.

TECHNICAL FIELD

The present invention relates to a method for more efficiently inducing a somatic embryo population having higher quality as compared with conventional procedures, comprising increasing a rate of single somatic embryos obtained from a somatic embryo mass of a plant.

BACKGROUND ART

For propagation of plants, various methods such as seeding, cuttage, division or suckering, tuber, bulb, and tuberous root have been employed. However, where the clonal propagation is sought, among tissue culture methods, in particular use of a propagation method utilizing a somatic embryo has been demanded, and in some occasions, its practical use has been examined (Pramod et al., Scale-up and automation in plant propagation: 76-93, 1991, Academic Press, Inc.). In conventional methods for inducing a somatic embryo, however, because the induced somatic embryo population frequently contains a high rate of somatic embryo masses (Mamiya and Sakamoto, J. of Plant Physiol., 159: 553-556, 2002; Chi et al., Biotechnology and Bioengineering 50: 65-7; and Chi et al., Biotechnology and Bioengineering 50: 65-72, 1996), a variety of means to recover a single somatic embryo which is more suitable for mass propagation have been proposed. However, the somatic embryo mass which occupies a high rate of somatic embryo population has not been actively utilized except plant species capable of permitting a multiple shoots body, resulting in a big problem in improving propagation efficiency. Even for plants in which an example of inducing a somatic embryo is known, the above situation is one of big factors responsible for a reason that the clonal propagation using the somatic embryo cannot be realized.

As a method for recovering a single somatic embryo from a somatic embryo population, a technique for screening a somatic embryo having a certain size or less and naturally passing through the openings of a mesh using the mesh without physical treatment (Nadel et al., Plant Cell, Tissue and Organ Culture 20: 119-124, 1990) and a technique of screening utilizing image analysis (Padmanabhan et al., Plant Cell Reports 17: 681-684 and Harrell et al., Acta Horticulturae 319: 595-600, 1992) have been proposed. However, these techniques primarily employ a method in which an existing single somatic embryo is simply screened from a somatic embryo population. As described above, the method for recovering a single somatic embryo from the somatic embryo mass which occupies a high rate of somatic embryo population is not contemplated. In the meantime, by modifying the composition of a medium for inducing a somatic embryo, an attempt to enhance an efficiency of inducing a single somatic embryo has been made in order to yield a certain outcome (Mamiya and Sakamoto, J. of Plant Physiol., 159: 553-556, 2002 and Dai, In Vitro Cell. Dev. Biol.-Plant 40: 376-383, July/August 2004). However, a procedure actively utilizing a somatic embryo mass, for which a universal technique common to many plants is sought, has not been reported so far, wherein the procedure comprises efficiently inducing a single somatic embryo.

A straining method utilizing a mesh has been applied to a callus (a kind of cultured cell) in some cases, and has achieved a certain effect such as an improvement in efficiency of somatic embryogenesis (Noguchi, Bulletin of the Tokyo Agricultural Experiment Station 27: 1-8, 1997 (Japan)). A cultured cell such as a callus is different from a somatic embryo, and constitutes an undifferentiated tissue. Since the tissue unit is small and the binding affinity between the tissues is weak, the damage due to division is small. However, the somatic embryo is a definitely differentiated tissue, and a method for physically dividing a somatic embryo mass is easily predicted to have extremely large damage to the tissue. Hence, there is no example that this division method has been examined.

As a method of utilizing the somatic embryo mass, known is a method comprising subjecting a somatic embryo mass to a germination process utilizing a solid medium, etc.; and dividing the somatic embryo mass into individual seedlings after the germination. However, such division operation would consume labor and time, resulting in high costs. Accordingly, the applicable plant species remains limited. In addition, although separation of the somatic embryos one by one from the somatic embryo mass may be allowed in some conditions, this technique would produce more troublesome operation compared with the case of dividing a germinating body, so that the technique is not a practical method.

SUMMARY OF INVENTION

It is an object of the present invention to solve problems with conventional methods for growing a somatic embryo of plants in which a somatic embryo induced from a callus exhibits a massive tissue (referred to as a "somatic embryo mass"), especially plants in which use of the somatic embryo mass is difficult without inducing into a single somatic embryo, thus to provide a method capable of inducing a high-quality somatic embryo at high efficiency.

As a result of intensive research, the present inventor has now found the following: (1) production of a single somatic embryo can be achieved by physically dividing a somatic embryo mass; (2) when a physical division such as a straining method, preferably a straining method utilizing a mesh, is used for the foregoing division, production of the somatic embryo with less damage is accomplished; further (3) recultivation of the somatic embryo as obtained by the physical division in a specific culture condition enables a large, uniform, and high-quality somatic embryo to be induced, the somatic embryo being not observed in conventional methods; and (4) addition of at least one of gibberellin and abscisic acid to the above medium (3) allows the quality of the resulting somatic embryo to be improved. Thus, the present inventor has now completed the present invention.

Thus, as a summary, the present invention includes the following features.

An aspect of the present invention provides a method for inducing a single somatic embryo, comprising physically dividing a somatic embryo mass of a plant.

The term "somatic embryo mass" used herein refers to a tissue in which many somatic embryos induced from a plant embryogenic callus have assembled so as to become massive. An embodiment of the present invention can preferably use a somatic-embryo-mass-forming plant for which use of the somatic embryo mass is difficult unless the mass is divided into individual somatic embryos. The somatic embryo mass as used in the present invention is preferably rich in a heart-shaped embryo and/or a torpedo-shaped embryo.

The "physical division" as used herein includes physically dispersing a somatic embryo mass into individual somatic embryos (i.e., single somatic embryos), specifically by manually or mechanically applying force to the somatic embryo mass. At this occasion, the somatic embryos include intact and/or damaged somatic embryos. The damage of the somatic embryo may occur either in an entire body or a part. The damage occurs, for example, due to a mechanical action such as pressure, sheer force, and cutting. The damage roughly has a degree to which the damage can be repaired by culturing the injured somatic embryos and a substantially normal somatic embryo can be induced. Thus, the physical division is preferably a division such that a substantially normal somatic embryo can be induced by culture after the division.

In an embodiment of the present invention, the physical division is preferably performed by straining, crushing, or cutting a somatic embryo mass.

The straining refers to a technique in which a somatic embryo mass is pressed onto a mesh or an equivalent instrument (or a device) and the individual somatic embryos are made to pass through openings, the used mesh or instrument having openings through which a single somatic embryo passes.

The crushing refers to a technique in which a somatic embryo mass is disintegrated by crushing the mass by using the twisted or flat surface of an instrument such as, for example, a scoopula, a spoon, and a spurtle.

The cutting refers to a technique in which a somatic embryo mass is randomly cut by using a knife such as a scalpel. The cutting should be carried out to a degree that a substantially normal somatic embryo can be induced when the resulting tissue and/or somatic embryo is cultured.

The above dividing enables a percentage of the single somatic embryo to increase. Previously, a method for simply collecting a free somatic embryo contained together in a somatic embryo mass induced from a callus by using a mesh has been known. However, the present invention provides a novel method for dividing a somatic embryo mass into individual somatic embryos. This method enables the rate of the single somatic embryo to markedly increase.

In another embodiment of the present invention, a method according to the present invention may further comprise culturing a tissue or somatic embryo obtained by division; and obtaining a somatic embryo having an improved quality.

This method is preferably carried out by culture in a plant culture medium containing gibberellin and/or abscisic acid.

In addition, the culture is preferably performed under the presence of carbon dioxide having a level exceeding the ambient level.

The present invention further provides a method for mass propagation of a plant comprising inducing a large number of single somatic embryos from a somatic embryo mass according to the above method; and causing the somatic embryos to germinate.

According to an embodiment of the present invention, this method may further comprise subjecting an induced somatic embryo to a dehydration process. The dehydrated somatic embryo can be stored without affecting its germination for about 1 to 3 months.

Another embodiment of the present invention may further comprise treating the dehydrated somatic embryo with gibberellin and/or abscisic acid before germination. This treatment enables the germination rate of the dehydrated somatic embryo to markedly increase.

A method of the present invention allows the rate of single somatic embryos suitable for mass propagation to increase, and further allows large, uniform, and high-quality somatic embryos to be induced by culturing a tissue being subjected to division. The enlarged somatic embryos can be so easily handled in a subsequent step including a germination step, and the germination rate increases.

The present specification incorporates the content described in the specification and/or the drawings of Japanese Patent Application No. 2008-321557 to which the present application claims priority.

BRIEF DESCRIPTION OF DRAWINGS

The patent or application file contains at least one drawing executed in color. Copies of this patent or patent application publication with color drawing(s) will be provided by the Office upon request and payment of the necessary fee.

MODE FOR CARRYING OUT THE INVENTION

Figure 1:
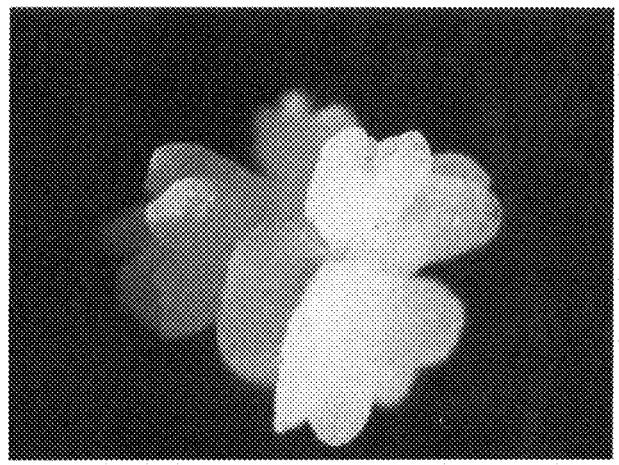
FIG. 1 shows a shape of a somatic embryo mass (I) (containing heart-shaped embryos) before straining.

Hereinafter, the present invention is further illustrated in detail.

The present invention provides a method for more efficiently producing a higher-quality somatic embryo population than conventional procedures, comprising increasing a percentage of a single somatic embryo by physically dividing a somatic embryo mass. This method enables plant mass propagation utilizing a somatic embryo to be efficiently carried out in a larger variety of plants.

<Plants>

The present invention can apply to any plants which provide a somatic embryo mass. Examples of the plants preferably include, but are not limited to, plants belonging to Hamamelidaceae, Cupressaceae, Pinaceae, Leguminosae, Myrtaceae, Salicaceae, Moraceae, Apiaceae, Araceae, Poaceae, Liliaceae, or Convolvulaceae, more preferably Hamamelidaceae (e.g. a plant belonging to Hamamelidaceae Liquidambar), and most preferably sweetgum.

Examples of the above plants are as follows: Hamamelidaceae (e.g., sweetgum), Cupressaceae (e.g., hinoki cypress), Pinaceae (e.g., pine), Leguminosae (e.g., alfalfa and acacia), Myrtaceae (e.g., eucalyptus), Salicaceae (e.g., poplar), Moraceae (e.g., a rubber tree), Apiaceae (e.g., carrot and celery), Araceae (e.g., spathiphyllum), Poaceae (e.g., rice), Liliaceae (e.g., asparagus), and Convolvulaceae (e.g., sweet potato).

<Induction of Embryogenic Callus>

Conditions in which an embryogenic callus is induced from various explants such as a leaf and a leaf stem of various plants used in the present invention are not particularly limited, and publicly known information can be used for the conditions. For example, conditions described in Agriculture, Forestry and Fisheries Research Literature Solution No. 17 Plant Biotechnology, 1991 (Japan), and WO2007/064028, etc., can be employed.

<Induction of Somatic Embryos/Somatic Embryo Masses from Embryogenic Callus>

Conditions of inducing somatic embryos/somatic embryo masses from the embryogenic callus as described above used in the present invention are not particularly limited, and publicly known information can be used. For example, conditions described in Agriculture, Forestry and Fisheries Research Literature Solution No. 17 Plant Biotechnology, 1991 (Japan), and WO2007/064028, etc., can be employed. It is notable that conditions using either a solid medium or a liquid medium are applicable, but the conditions using a liquid medium allow the collection of the somatic embryos/somatic embryo masses to be more readily achieved. In addition, the lighting conditions are not particularly limited. However, since the binding strength between the somatic embryos/somatic embryo masses is lower for the somatic embryos/somatic embryo masses induced in a dark place, the dark conditions allow a subsequent physical division to be more readily achieved.

<Developing Stage of Somatic Embryo Mass and Division>

For a case of the induced somatic embryo mass, the mass preferably contains a larger number of heart-shaped embryos or torpedo-shaped embryos at a developing stage than spherical-shaped embryos. Most preferably, the mass contains a large number of the torpedo-shaped embryos. A larger number of spherical-shaped embryos at the preceding stage are not preferable because of delay, etc., in germination after the division of the somatic embryo mass. In contrast, a large number of tyledonary embryos at the later stage promote growth and the size becomes big. Accordingly, it is not preferable because the damage at the division of the somatic embryo mass is large. In order to make such a condition that a large number of heat-shaped embryos or torpedo-shaped embryos are contained, a condition in which the embryos are cultured in a medium to which at least one of amino acids (e.g., glutamine and asparagine) and a caseinase-digested product is added is effective. The somatic embryo mass containing a large number of heart-shaped embryos or torpedo-shaped embryos at a developing stage, as suitably obtained herein, has many masses having a size of 0.5 to 15 mm depending on conditions of inducing somatic embryos/somatic embryo masses from the embryogenic callus and on types of plant species. Examples of the physical division of the foregoing somatic embryo mass used as a main subject include methods utilizing random cutting using a scalpel, straining using a mesh, crushing using a scoopula and the like. Any of them can be used. However, as a condition in which a single somatic embryo with the least damage is readily obtained, the straining using a mesh can be preferably exemplified. For the respective procedures, the optimal condition to generate the single somatic embryo is designed depending on the types of the plant species. The optimal condition is selected by observing a tissue collected by various processing conditions under a stereoscopic microscope and by setting to conditions in which a single somatic embryo with the least damage can be obtained. Alternatively, the conditions can be selected based on a percentage of the single somatic embryo in the somatic embryo population collected after recultivation of the processed tissue and on the size and uniformity of the somatic embryo.

Among the physical divisions of the induced somatic embryo mass, the used mesh size of a mesh is important for the straining method using a mesh. The appropriate mesh size is selected depending on the types of plant species and the size of induced somatic embryo/somatic embryo mass. In the case of using openings having a size smaller than an appropriate size, the damage to the somatic embryo becomes excessive, and the ability of germinating the somatic embryo decreases. In the case of using openings having a size larger than an appropriate size, the division of the somatic embryo mass is insufficient, and the rate of single somatic embryos decreases. Depending on the types of plant species and the size of somatic embryo/somatic embryo mass, a mesh having a mesh size of 0.6 to 4.0 mm, preferably 1.0 to 2.0 mm, is employed. A sieve in which a mesh made of stainless is incorporated is suitable for the straining work.

The specific procedures of the straining method are as follows: (1) Place a suitable amount of the induced somatic embryo/somatic embryo mass onto the mesh of a sieve; (2) Completely strain the somatic embryo/somatic embryo mass while crushing the mass using a scoopula or spoon to such a degree that the tissues do not remain on the mesh; and (3) Collect the divided tissues which have passed through the mesh into another container. When the appropriate mesh size of the mesh is selected, the collected tissues contain a large number of single somatic embryos having less damage. These embryos can be directly used in the germination step. The conditions for the germination step may be the same conditions as those for somatic embryos improved through the recultivation step (as described below). However, although the somatic embryos contained in the strained tissues are single, the size of the embryos is extremely small, and a part of the embryos contain damaged somatic embryos. Thus, it is preferable to undergo the recultivation step.

Among the means of physically dividing induced somatic embryo mass, the random cutting using a knife such as a scalpel does not require special conditions regarding the direction or strength of the cutting. The random cutting can be performed using a scalpel used for conventional tissue culture. As to the dividing size, a preparatory study is preferably carried out to determine the dividing size because the size depends on the types of the plant species and the condition of the somatic embryo mass.

Among the means of physically dividing induced somatic embryo mass, in the crushing using a scoopula or the like, there is no limitation except that the maximal strength of the crushing is examined in a preparatory study. Preferably, the bottom of the scoopula is made to press onto the somatic embryo mass, and the crushing is carried out by applying force in such a manner as to enable the somatic embryo mass to be disintegrated. Other than the scoopula, a spoon, a spatula, or a spurtle, etc., can be used.

<Recultivation of Tissue which has been Obtained by Physical Division of Induced Somatic Embryo Mass>

A tissue which has been obtained by the physical division of the induced somatic embryo mass is recultivated under appropriate conditions. The recultivation allows the somatic embryo to be markedly enlarged, which more clearly exerts an effect achieved by the physical division (i.e., an improvement in the percentage and uniformity of the single somatic embryo). The enlarged somatic embryo is extremely easily handled in a subsequent step including a germination step, and the germination rate also increases. The recultivation further increases the uniformity of the somatic embryo as well. In addition, the somatic embryos which have been damaged in the step of the division become normal during the recultivation in many cases. The percentage of the single somatic embryo further increases.

The conditions used for the recultivation are selected from various culture conditions used for conventional plant tissue culture, and such conditions comprise inhibition of excessive rooting and germination of the tested somatic embryo, thereby leading to both the enlargement of the size of the somatic embryo and the increase in the percentage and uniformity of the single somatic embryo. As a plant growth regulator (PGR) to be added, a sole use or a combination of gibberellin and abscisic acid is particularly effective.

The recultivation medium employs a basic medium used for conventional tissue culture such as MS medium (Physiol. Plant., 15, p 143, 1962). The medium having a conventional concentration or 0.1 to 0.9-fold diluted medium is used. As a sugar source, sucrose having a concentration of 0.5 to 4%, and preferably 1 to 3% is used. In addition, as another sugar, sorbitol or mannitol having a concentration of 0.5 to 6%, and preferably 1 to 4% may be added. A high concentration of the basic medium or sucrose allows the storage property of the collected somatic embryo to decrease after dehydration. Gibberellin, a plant growth regulator, is added at a concentration of 0 to 1 ppm, preferably 0.01 to 0.1 ppm. Gibberellin exhibits a high effect in the enlargement of the size and uniformity of the divided (single) somatic embryos. In addition, 0 to 1 ppm and preferably 0.01 to 0.1 ppm of abscisic acid may be added. A combination of appropriate concentrations of gibberellin and abscisic acid exerts an effect of preventing a decrease in the ability of temporally germinating the somatic embryo, the decrease occurring in some conditions. Furthermore, as cytokinins, 0 to 0.5 ppm and preferably 0.01 to 0.2 ppm of 6-benzyladenine (BA) may be used. Examples of the other cytokinins that are appropriately selected to be used can include zeatin (ZEA), kinetin (KN), 6-(benzylamino)-9-(2-tetrahydropyranyl)-9H-purine (PBA), 2-isopentenyl adenine (2ip), thidiazuron (TDZ), and the like. As a buffer, 0.1 to 10 mM of MES may be added. The pH of the medium is set to between 5 and 7.

The light environment uses light conditions (i.e., day length, 12 to 16 hours; and photosynthetic photon flux density, 5.7 to 34.2 $\mu mole/m^2/sec$). For plant species having strong photosensitivity, the conditions of a daylength of 12 to 16 hours and a photosynthetic photon flux density of less than 5.7 $\mu mole/m^2/sec$, or dark conditions, may be used.

The temperature is between 20° C. and 30° C., and preferably between 23° C. and 27° C. The culture period is between 5 and 40 days, and preferably between 10 and 20 days. When the shaking culture is carried out using a flask, the rotating speed is between 50 and 150 rpm, and preferably between 60 and 100 rpm. A culture tank with stirring or an air lift system can be used. In this case, the ventilation volume is between 0.001 and 0.5 vvm, and preferably between 0.01 and 0.2 vvm.

The recultivation may be carried out under carbon dioxide-rich environment. The concentration of carbon dioxide is 0.1 to 10%, preferably 0.5 to 3%. A medium used for conventional tissue culture such as MS medium is used as a basic medium, and the medium having a conventional concentration or 0.1 to 0.9-fold diluted medium is used. As a sugar source, 0 to 2% and preferably 0.05 to 1% of sucrose may be added. As another sugar, sorbitol or mannitol may be used at a concentration of 0.5 to 6%, preferably 1 to 4%. The conditions other than that are the same as the above.

Any of the conditions prefers liquid culture, but a solid medium which is solidified by agar or Gelrite may be used. For this condition, the agar has a concentration of 0.6 to 2% and preferably 0.8 to 1.2%, and the Gelrite has a concentration of 0.1 to 0.5% and preferably 0.2 to 0.4%. As long as the culture container employs those used for conventional tissue culture, there is no particular limitation.

<Dehydration of Somatic Embryo>

The recultivated somatic embryo can be subjected to a germination step as it is. When storage is needed, dehydrating the somatic embryo enables the storage for a certain period. A container in which the dehydration is carried out is not particularly limited. However, in the case of processing a small amount, a dish (e.g., diameter, 9 cm; and height, 1.5 cm) is used. In the case of processing a large amount, a transparent box-shaped plastic container (e.g., size, about 22 cm×17 cm×7 cm) is used. In any of the cases, a paper towel was placed at the bottom, and an appropriate amount of the somatic embryo is put on the paper (for a 9-cm dish, about 1 to 20 g; and for the above box-shaped container, about 30 to 100 g). As to the light environment, light conditions (i.e., daylength, 12 to 16 hours; and photosynthetic photon flux density, 1.1 to 34.2 $\mu mole/m^2/sec$, preferably 3.4 to 22.8 $\mu mole/m^2/sec$) may suitably be used, or alternatively the usable light conditions may have a daylength of 12 to 16 hours and a photosynthetic photon flux density of less than 3.4 $\mu mole/m^2/sec$, or dark conditions can be allowed. The temperature is between 20° C. and 30° C., and preferably between 23° C. and 27° C. The period is set to between 1 day to 20 days, and preferably between 2 days and 10 days. The somatic embryo that has completed dehydration can be stored at a low temperature of about 4° C. in the dark while placing it in a 9-cm dish in which a paper towel is put at the bottom. Although depending on plant species, the storage does not impart damage to the germination of the somatic embryo after storage for about 1 to 3 months.

<Germination of Somatic Embryo>

The somatic embryos or dehydrated somatic embryos as obtained above can highly efficiently germinate on a solid medium or in a liquid medium. Accordingly, they are suitable for mass propagation of the plant clones. Use of the liquid medium is preferable for the purpose of the mass propagation. A medium used for the germination is a basic medium such as MS medium supplemented with 1 to 6%, preferably 2 to 4%, of sucrose as a sugar source is added. In the case of very active rooting, as another sugar, sorbitol or mannitol may be added at a concentration of 1 to 6%, preferably 2 to 4%. While a plant growth regulator is not particularly required to be added, auxins or cytokinins may be added to promote the germination. The pH of the medium is between 5 and 7. The light environment comprises light conditions having a daylength of 12 to 16 hours and a photosynthetic photon flux density of 1.1 to 34.2 $\mu mole/m^2/sec$, preferably 2.3 to 11.4 $\mu mole/m^2/sec$. The temperature is between 20° C. and 35° C., preferably between 25° C. and 30° C. In the case of a solid medium, agar (0.8 to 1.2%) or Gelrite (0.1 to 0.5%) is used to solidify the medium. As long as the container is for plant tissue culture, there is no particular limitation. However, in the case of a solid medium, the plant box as described above is used, and in the case of a liquid medium, various culture tanks are used. Undergoing the dehydration step may temporally reduce the ability of germinating a somatic embryo depending on the conditions (types of plant species, and quality of somatic embryo subjected to recultivation). In that case, by performing a method for adjusting a concentration of PGR (in particular, gibberellin and abscisic acid) included in the recultivation medium or a method for immersing the post-dehydrated somatic embryo into a gibberellin solution for a certain period, the germination ability can be quickly recovered.

<Transfer to Greenhouse>

A plant body which has been redifferentiated from the somatic embryo is picked up from a culture container and normally grows in a greenhouse. A culture soil used for transplantation is not particularly limited, but may employ a commercially available culture soil used for rearing of seedlings. After transplantation of the plant body, appropriate humidification and shading are preferably carried out for about 1 to 3 weeks.

Hereinafter, the present invention is further illustrated in detail by referring to Examples. However, these Examples do not limit the scope of the present invention. It is notable that unless otherwise specified, the pH of the medium used in the respective Examples and Comparative Examples was adjusted to 5.6 with 0.01 N or 0.1 N hydrochloric acid or sodium hydroxide aqueous solution before sterilization by using an autoclave following formulation of various components. Then, autoclaving was performed at 121° C. for 15 minutes. Four culture containers were used for a same experiment. The number/amount of the germinating bodies or somatic embryos and the numeral of the germination rate were designated as their average.

EXAMPLES

Hereinafter, the present invention is described by referring to Examples. However, the technical scope of the present invention is not limited by these Examples.

Example 1

Figure 2:
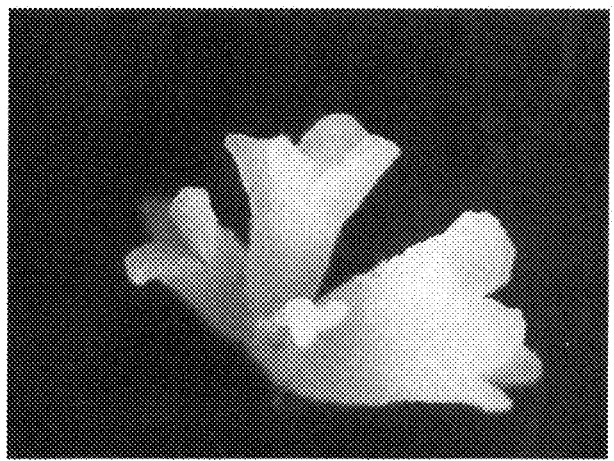
FIG. 2 shows a shape of a somatic embryo mass (II) (containing torpedo-shaped embryos) before straining.

Culture cells (an embryogenic callus, hereinafter referred to as an "EC") of sweetgum (*Liquidambar styraciflua*, a line of Top Gum) obtained from ArborGen Corp., U.S., were used as a test material. The conditions of inducing an EC from the explant were according to U.S. Pat. No. 5,840,581. The following studies were carried out by using the method of Dai et al. (In Vitro Cell. Dev. Biol.-Plant 40: 376-383, July/August 2004) as culture conditions including the maintenance of the EC. The EC subcultured on agar maintenance medium (IMM agar medium, Table 1) was cultured in a liquid maintenance medium (IMM liquid medium) to yield an EC used for induction of a somatic embryo. Although Dai et al. induced a somatic embryo on a solid medium (DM agar medium, Table 2), the medium used in this Example (DMMA liquid medium) was a medium in which 5 mM MES, 5 mM glutamine, and 5 mM asparagine were added to a liquid medium devoid of agar (DM liquid medium) was used. Seven hundreds of the EC prepared according to the method of Dai et al. following collection from the IMM liquid medium were placed in a 300-ml Erlenmeyer flask having 100 ml of DMMA liquid medium dispensed. The EC was cultured with shaking (80 rpm) at 25° C. in the dark for 6 weeks to induce somatic embryos. Most of these induced somatic embryos were in a massive form having a size of 2-7 mm. The developing stage of the somatic embryos contained in the mass was a stage ranging from a heart-shaped embryo to a torpedo-shaped embryo (FIG. 1 and FIG. 2). The residual moisture of the somatic embryo collected was absorbed with a paper towel. The somatic embryo was placed in a box-shaped plastic container (in which the size was 22 cm×17 cm×7 cm, and a paper towel was put at the bottom), and was dehydrated at 25° C. in the dark for 3 days.

Figure 3:
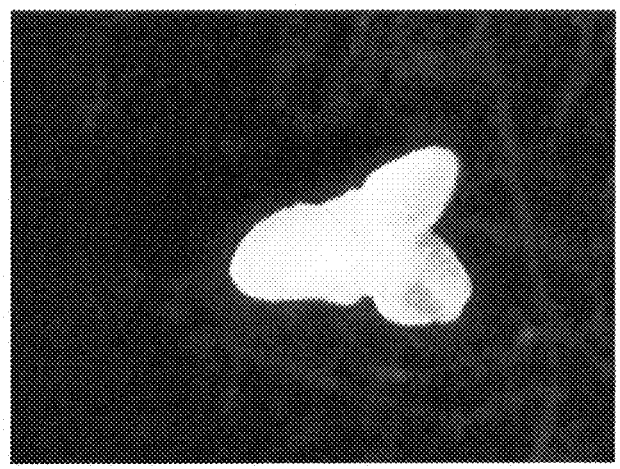
FIG. 3 shows a healthy (or normal) somatic embryo (I) after straining.
Figure 4:
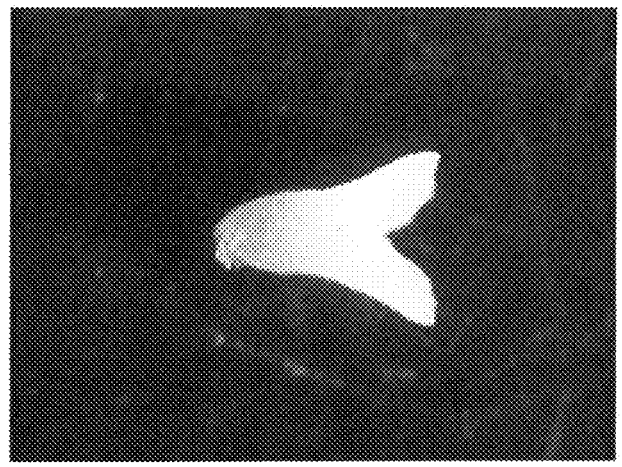
FIG. 4 shows a healthy (or normal) somatic embryo (II) after straining.
Figure 5:
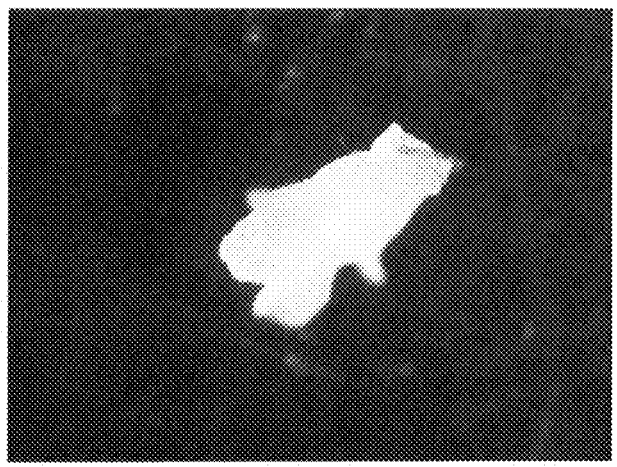
FIG. 5 shows a lightly damaged somatic embryo after straining.
Figure 6:
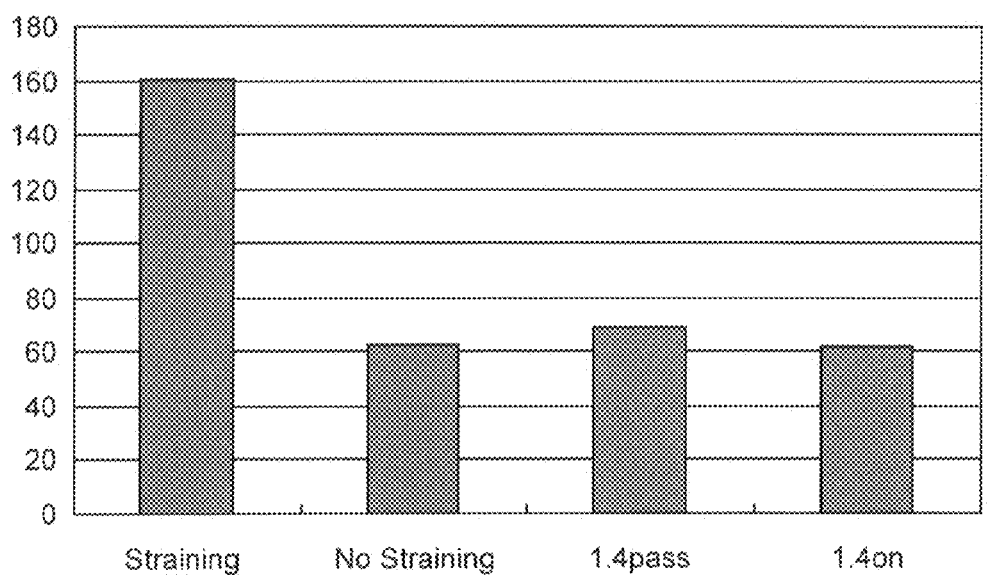
FIG. 6 indicates an influence of straining on production of a germinating body. The ordinate represents the number of germinating bodies per gram of a tested dehydrated somatic embryo material. As to 1.4 pass and 1.4 on, see Comparative Example 2.

Next, 4 g of the dehydrated somatic embryo mass was placed on a sieve with a mesh having a mesh size of 1.4 mm, the sieve having a diameter of 15 cm and a depth of 6 cm. The mass was completely strained using a scoopula in such a manner that the somatic embryo mass was not left on the mesh. The tissues clogged in the openings of the mesh were made to pass through the openings as possible as it could by applying vibration. The strained tissues were primarily composed of single healthy (or normal) somatic embryos (FIG. 3 and FIG. 4). The results demonstrated that the straining method allowed the single somatic embryos to be effectively produced from the somatic embryo mass. Some of them were observed as damaged somatic embryos (FIG. 5); however, the degree of the damage was negligible, and even those somatic embryos were single. The strained tissue collected was weighed, and had a weight of 2.7 g. Then, 0.1 g of the tissue was each placed in a plant box in which 50 ml of 2% sucrose-containing ½ MS medium solidified with 0.8% agar (pH 5.8; hereinafter, referred to as a "germination medium") was added. The tissues were cultured at 25° C. under a light place (daylength, 16 hours; and photosynthetic photon flux density, 5.7 $\mu mole/m^2/sec$) for 8 weeks to yield germination bodies but not multiple shoots bodies. The number of the germinating bodies per g of the dehydrated somatic embryo mass tested was 161 (FIG. 6, "Straining").

Comparative Example 1

Under the same conditions as in Example 1, the dehydrated somatic embryo mass, but not strained, was placed in the germination medium. Although the germinating bodies were obtained, most of them were multiple shoots bodies. In addition, the number of the germinating bodies per g of the dehydrated somatic embryo mass was 63 (FIG. 6, "No Straining").

Comparative Example 2

Under the same conditions as in Example 1, after the dehydrated somatic embryo mass was placed on the sieve, vibration was applied without straining. Then, the tissues that had passed through a mesh (1.4pass) were distinguished from the tissues that had been left on the mesh (1.4 on). The respective tissues were placed in the germination medium, and the number of germinating bodies was counted. The number of the germinating bodies per g of the dehydrated somatic embryo mass tested was 69 for 1.4pass, and 62 for 1.4 on. Among them, most of the germinating bodies of 1.4 on were multiple shoots bodies.

Example 2

Figure 7:
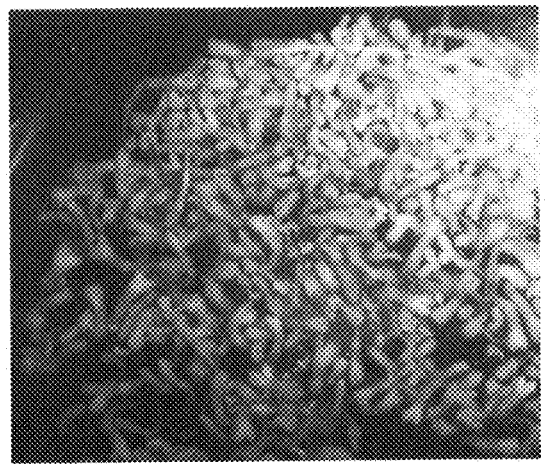
FIG. 7 shows an enlarged somatic embryo (an improved somatic embryo) by recultivation.
Figure 8:
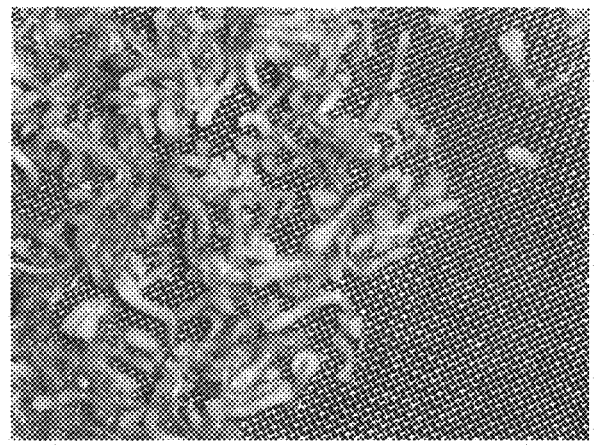
FIG. 8 shows an enlarged somatic embryo (an improved somatic embryo) collected.
Figure 9:
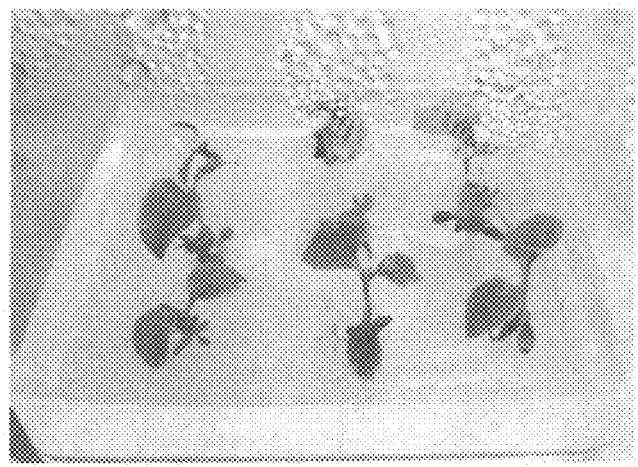
FIG. 9 shows a germinating body derived from an improved somatic embryo.
Figure 10:
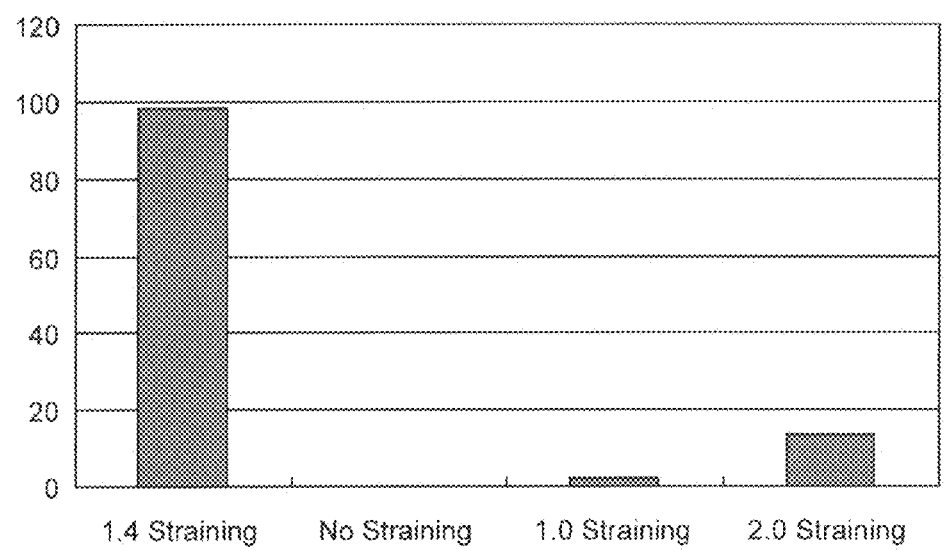
FIG. 10 indicates an influence of a straining and recultivation step on production of an improved somatic embryo. The ordinate represents the number of improved somatic embryos per gram of a tested dehydrated somatic embryo material. As to 1.4 Straining, see Example 2. In addition, as to 1.0 Straining and 2.0 Straining, see Example 3.
Figure 11:
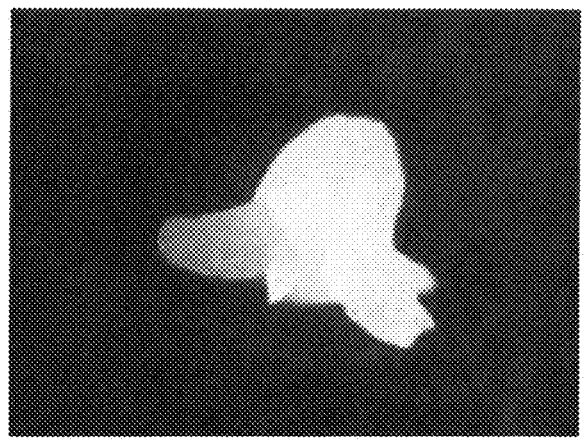
FIG. 11 shows a shape of a randomly cut somatic embryo (I).
Figure 12:
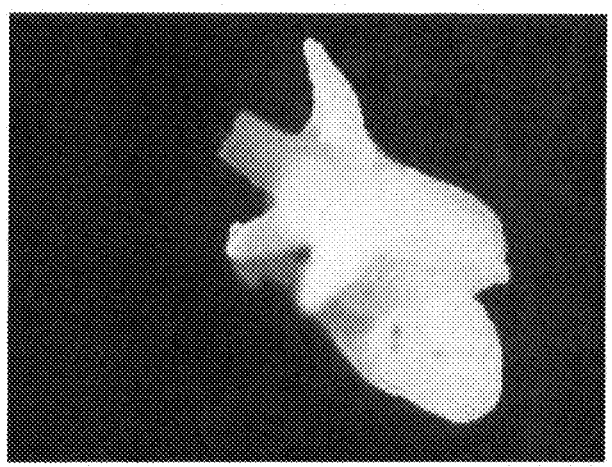
FIG. 12 shows a shape of a randomly cut somatic embryo (II).
Figure 13:
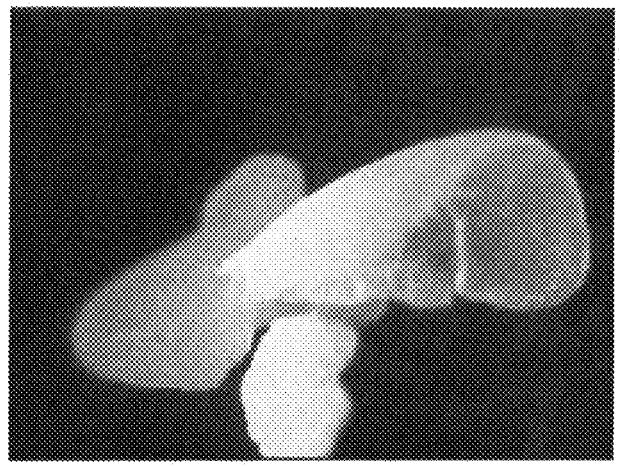
FIG. 13 shows a shape of a crushed somatic embryo (I).
Figure 14:
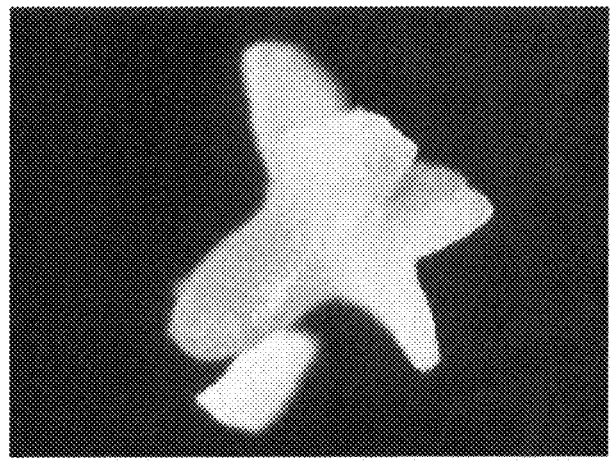
FIG. 14 shows a shape of a crushed somatic embryo (II).

First, 0.15 g of the strained tissue as obtained under the same conditions as in Example 1 was each placed in a 300-ml flask to which 100 ml of ½-fold diluted DM liquid medium containing 2% sucrose and 0.02 ppm gibberellin (pH 5.6; hereinafter, referred to as "recultivation medium 1") was added. The tissues were cultured with shaking (80 rpm) at 25° C. in a light place (daylength, 16 hours; and photosynthetic photon flux density, 22.8 µmole/m$^2$/sec) for 12 days. The single somatic embryos contained in the strained tissues during the culture were enlarged, and formed a population of torpedo-shaped embryos having more increased uniformity (i.e., improved somatic embryos, FIG. 7 and FIG. 8). This result demonstrated that the recultivation step was extremely effective for improving the quality of the somatic embryos. These improved somatic embryos having high quality were able to be readily handled with a forceps, so that performance in operation was markedly enhanced compared to the single somatic embryos having small size obtained immediately after straining. The number of these improved somatic embryos per flask was counted, and the number per g of the dehydrated somatic embryo mass tested was 98 (FIG. 10, "1.4 Straining"). These improved somatic embryos germinated on the germination medium with high efficiency of 80% or more (FIG. 9).

Comparative Example 3

Under the same conditions as in Example 2, the dehydrated somatic embryos, but not strained, were cultured using the recultivation medium. However, the high-quality somatic embryos similar to those of Example 2 were not obtained at all (FIG. 10. "No Straining").

Comparative Example 4

Under the same conditions as in Example 2, the recultivation was carried out using a medium without gibberellin. The high-quality somatic embryos similar to those of Example 2 were not obtained at all.

Example 3

The experiment of Example 2 was carried out using a sieve with a mesh having a mesh size of 1.0 mm or 2.0 mm. The number of the obtained high-quality somatic embryos per g of the dehydrated somatic embryo mass tested was 2 or 13, respectively (FIG. 10, "1.0 Straining" and "2.0 Straining").

Example 4

Figure 15:
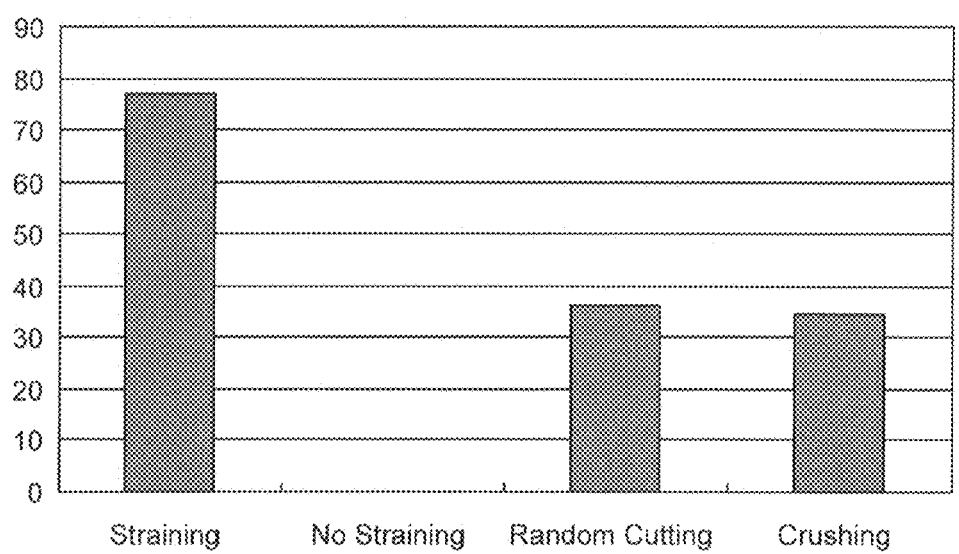
FIG. 15 indicates an influence of random cutting and crushing operations on production of an improved somatic embryo. The ordinate represents the number of improved somatic embryos per gram of a tested dehydrated somatic embryo material.

The experiment of Example 2 was carried out utilizing random cutting with a scalpel or by crushing with a scoopula as a procedure for dividing the dehydrated somatic embryo mass, in place of straining using a mesh. These post-processed somatic embryos were found to be slightly damaged compared to those of the straining method. However, any of them contained many single somatic embryos. Therefore, the effect of the physical division was recognized (FIG. 11 to FIG. 14). The number of the somatic embryos improved similar to those of the straining method recognized after the recultivation per g of the dehydrated somatic embryo mass tested was 36 for the random cutting method, and 35 for the crushing method (FIG. 15, "Random Cutting" and "Crushing").

Example 5

Figure 16:
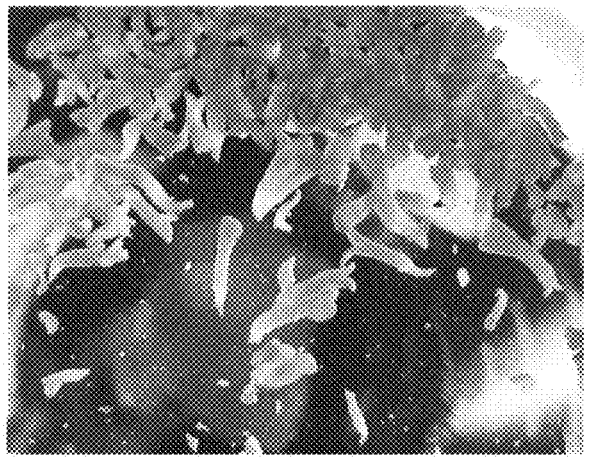
FIG. 16 shows an improved somatic embryo under $CO_2$-rich environment.

The experiment was carried out by changing only the recultivation conditions of Example 2 to the following conditions. As a basic medium, DM liquid medium (pH 5.8, "Recultivation medium 2") to which 0.1% sucrose, 2% sorbitol, 0.01 ppm gibberellin, and 0.01 ppm BA were added was used. Then, the culture environment was set to the condition having a $CO_2$ concentration elevated to 2%. The somatic embryos included in the strained tissue were improved similar to those of Example 2. Moreover, the chlorophyll formation was facilitated to such a degree that the color of the entire somatic embryo became green, and the more improvement in quality was recognized (FIG. 16).

Comparative Example 5

The recultivation of Example 5 was carried out under conventional environment conditions without allowing $CO_2$ to be rich. The changing rate of the somatic embryo was slow, and almost no changes were observed during the identical culture period.

Example 6

Figure 17:
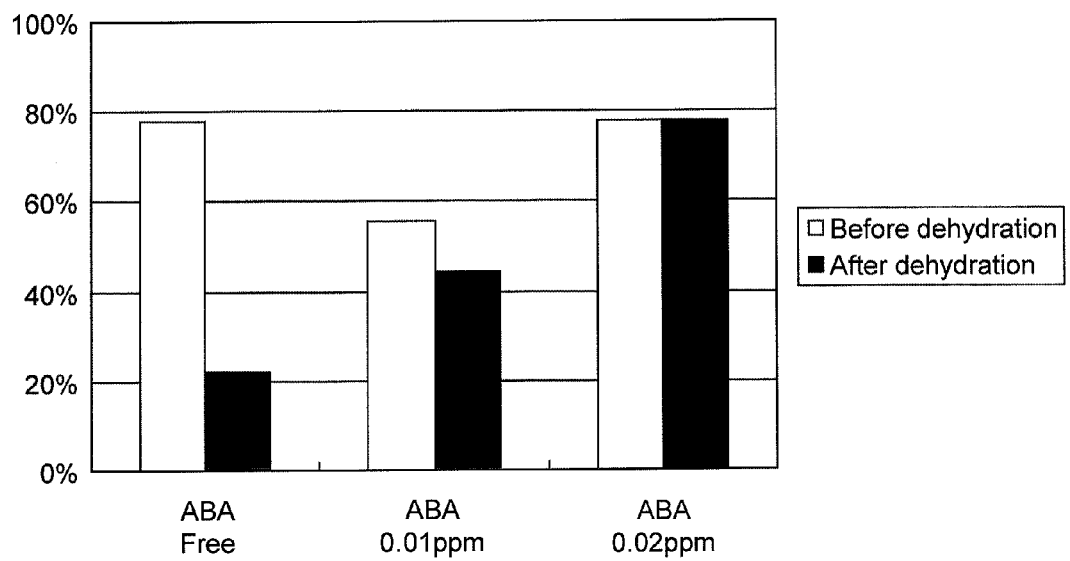
FIG. 17 indicates an influence of addition of abscisic acid (ABA) on the germination of an improved somatic embryo induced. The ordinate represents the germination rate after 7 weeks.

To the recultivation medium of Example 2 were added 0 ppm (no addition), 0.01 ppm, and 0.02 ppm of abscisic acid (ABA), and the improved somatic embryos were induced. These improved somatic embryos were used as they were (before the dehydration process) and the dehydration process was carried out (i.e., the excess medium contained in the improved somatic embryos collected was absorbed with a paper towel; the embryos were placed in a ϕ9-cm plastic dish in which a paper towel was put at the bottom; and the embryos were cultured at 25° C. for 2 days in the dark). Then, the embryos were made to germinate by using the method described in Example 1. After 7 weeks, the germination rate was determined. The germination rate of the post-dehydrated improved somatic embryo in ABA-free area decreased to ⅓ or less compared to that before the dehydration process. In contrast, the percentage in the decrease in the germination rate of the improved somatic embryos as obtained from the 0.01-ppm-ABA-added area was markedly reduced. For the improved somatic embryos obtained from the 0.02-ppm-ABA-added area, a difference in their germination rate before and after dehydration was not recognized. However, addition of ABA was demonstrated to be effective for preventing a decrease in the ability of germinating the improved somatic embryo (FIG. 17).

Example 7

Figure 18:
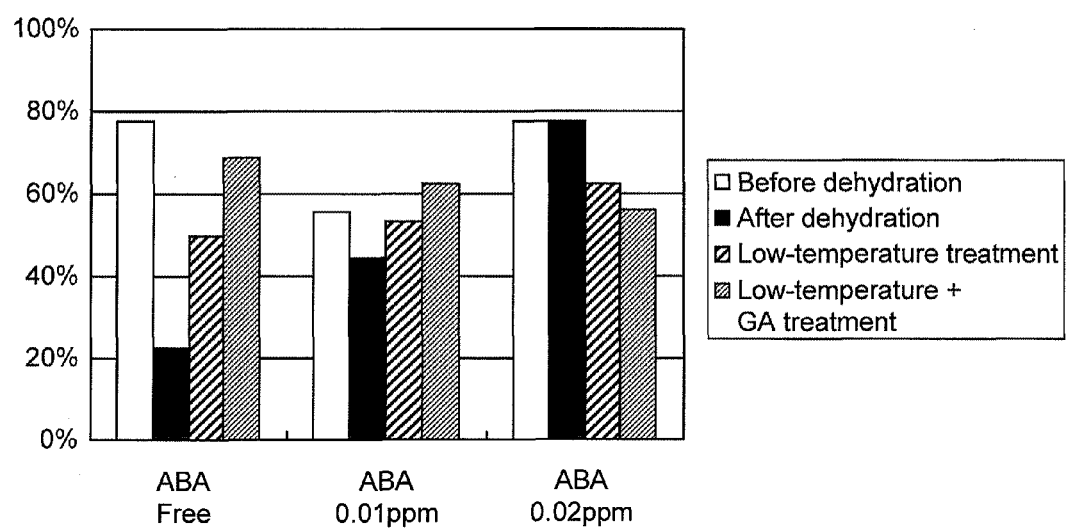
FIG. 18 indicates an influence of gibberellin (GA) treatment following dehydration and low-temperature storage on the germination of an improved somatic embryo. The ordinate represents the germination rate after 7 weeks.

The post-dehydrated improved somatic embryos as obtained in Example 6 were further stored at 4° C. in the dark for 1 month (low-temperature treatment), and were then immersed in a gibberellin solution for 10 minutes (low-temperature and GA treatment). After that, the embryos were placed in the germination medium, and the germination rate after 7 weeks was determined. The improvement in the germination rate was recognized in the ABA-free area and the 0.01-ppm-ABA area. Although there is a report that low-temperature treatment increased the germination rate, it was confirmed that this treatment exerts an effect of further improving the germination rate (FIG. 18).

TABLE 1

IMM Agar Medium Composition (pH 5.6)

| Components | mg/L |
|---|---|
| $KH_2PO_4$ | 300 |
| $KNO_3$ | 1,000 |
| $Ca(NO_3) \cdot 4H_2O$ | 500 |
| $MgSO_4 \cdot 7H_2O$ | 71.5 |
| KCl | 65 |
| $NH_4NO_3$ | 1000 |
| $MnSO_4 \cdot 4H_2O$ | 8 |
| $ZnSO_4 \cdot 7H_2O$ | 4 |
| $H_3BO_3$ | 2 |
| KI | 0.6 |
| $Na_2MoO_4 \cdot 2H_2O$ | 0.025 |
| $CuSO_4 \cdot 5H_2O$ | 0.025 |
| $CoCl_2 \cdot 6H_2O$ | 0.025 |
| Myo-Inositol | 100 |
| $Na_2EDTA$ | 0.0373 |
| $FeSO_4 \cdot 7H_2O$ | 0.0278 |
| Thiamine.HCl | 1 |
| Nicotinic Acid | 0.1 |
| Pyridoxine.HCl | 0.1 |
| L-glutamine | 550 |
| L-asparagine | 510 |
| L-arginine | 170 |
| 2,4-D | 2 |
| BA | 0.25 |
| Sucrose | 40,000 |
| Agar | 8 |

TABLE 2

DM Agar Medium Composition (pH 5.6)

| Components | mg/L |
|---|---|
| $KH_2PO_4$ | 300 |
| $KNO_3$ | 1,000 |
| $Ca(NO_3) \cdot 4H_2O$ | 500 |
| $MgSO_4 \cdot 7H_2O$ | 71.5 |
| KCl | 65 |
| $NH_4NO_3$ | 1000 |
| $MnSO_4 \cdot 4H_2O$ | 8 |
| $ZnSO_4 \cdot 7H_2O$ | 4 |
| $H_3BO_3$ | 2 |
| KI | 0.6 |
| $Na_2MoO_4 \cdot 2H_2O$ | 0.025 |
| $CuSO_4 \cdot 5H_2O$ | 0.025 |
| $CoCl_2 \cdot 6H_2O$ | 0.025 |
| Myo-Inositol | 100 |
| $Na_2EDTA$ | 0.0373 |
| $FeSO_4 \cdot 7H_2O$ | 0.0278 |
| Thiamine.HCl | 1 |
| Nicotinic Acid | 0.1 |
| Pyridoxine.HCl | 0.1 |
| Sucrose | 40,000 |
| Agar | 8 |

INDUSTRIAL APPLICABILITY

The present invention is industrially very useful in that plant mass propagation utilizing a somatic embryo can be achieved in plants for which use of a somatic embryo mass is difficult.

All the publications, patents, and patent applications cited herein are incorporated herein by reference in their entirety.

The invention claimed is:

1. A method for obtaining a single somatic embryo, comprising:
   physically dividing a somatic embryo mass of a plant by straining the somatic embryo mass through a mesh, to extrude at least one single somatic embryo; and
   obtaining the extruded single somatic embryo,
   wherein said straining occurs before germination.

2. The method according to claim 1, further comprising culturing a tissue or somatic embryo obtained by the physical division in a plant culture medium containing gibberellin and/or abscisic acid to obtain a large, uniform and quality-improved somatic embryo.

* * * * *